(12) United States Patent
Studer et al.

(10) Patent No.: US 10,238,287 B2
(45) Date of Patent: Mar. 26, 2019

(54) OPHTHALMOLOGICAL NEGATIVE-PRESSURE DEVICE AND PATIENT INTERFACE

(71) Applicant: Ziemer Ophthalmic Systems AG, Port (CH)

(72) Inventors: Thomas Studer, Neuchatel (CH); Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 182 days.

(21) Appl. No.: 15/151,187

(22) Filed: May 10, 2016

(65) Prior Publication Data

US 2016/0331231 A1 Nov. 17, 2016

(30) Foreign Application Priority Data

May 11, 2015 (EP) .................................... 15167073

(51) Int. Cl.
*A61B 3/00* (2006.01)
*A61B 3/10* (2006.01)
*A61B 3/15* (2006.01)
*A61F 9/009* (2006.01)

(52) U.S. Cl.
CPC .............. *A61B 3/152* (2013.01); *A61F 9/009* (2013.01)

(58) Field of Classification Search
CPC ............ A61F 2007/0054; A61F 7/0085; A61F 2007/0001; A61F 2007/0095; A61F 2007/0226; A61F 7/02; A61F 9/009

USPC ......... 351/200, 205, 206, 209–211, 221, 222
See application file for complete search history.

(56) References Cited

U.S. PATENT DOCUMENTS

| 2009/0118717 A1* | 5/2009 | Brownell | A61F 9/00827 606/4 |
| 2012/0272963 A1* | 11/2012 | Thomas | A61M 16/0666 128/204.23 |

* cited by examiner

*Primary Examiner* — Brandi Thomas
(74) *Attorney, Agent, or Firm* — Banner & Witcoff, Ltd.

(57) ABSTRACT

The invention relates to a negative-pressure device (1) for affixing a patient interface (2) with a negative-pressure cavity (20) onto a patient eye. The negative-pressure device (1) comprises a negative-pressure generator (10) and a pressure sensor (11) with a device-side pressure sensor interface (14) for coupling the pressure sensor (11) to the negative-pressure cavity in a manner fluidically separate from the negative-pressure interface (13). The negative-pressure device furthermore relates to a control unit (12) operatively coupled to the negative-pressure generator (10) and the pressure sensor (11), wherein the control unit (12) is designed to detect a faulty fluidic coupling of the negative-pressure cavity (20) by evaluating a pressure established by the pressure sensor (11). The invention furthermore relates to a patient interface (2) with a negative-pressure cavity (20), wherein the negative-pressure cavity (20) has a negative-pressure interface and a fluidically separate pressure sensor interface, as well as a patient interface with an integrated pressure sensor. The invention furthermore relates to a method for coupling a patient interface (2) to a patient eye.

7 Claims, 3 Drawing Sheets

OPHTHALMOLOGICAL NEGATIVE-PRESSURE DEVICE AND PATIENT INTERFACE

CROSS-REFERENCE TO RELATED APPLICATIONS

This application claims priority to European Patent Application 15 167 073.4 filed May 11, 2015, the disclosure of which is incorporated herein by reference in its entirety.

TECHNICAL FIELD

The present invention relates to devices and methods in the field of ophthalmology. The invention relates, in particular, to negative-pressure devices for coupling a patient interface onto a patient eye, and to patient interfaces. The invention furthermore relates to a method for coupling a patient interface onto a patient eye.

PRIOR ART

The use of radiation generators, in particular lasers, is known for the purposes of treating and/or diagnosing eye tissue. Corresponding devices such as ophthalmological laser apparatuses have, for example, a base device with a laser light source for generating laser pulses, for example femtosecond laser pulses, and an application head with a projection lens which is coupled to the patient eye for treatment purposes. The application head can be movably connected to the base device, for example by way of an articulated arm, wherein the articulated arm may simultaneously serve for optical beam guidance from the laser light source to the application head. By way of example, a corresponding arrangement is disclosed in EP 1731120. Moreover, there devices in which the application head is integrated into the base instrument or in which other device arrangements are provided.

Mechanical and optical coupling of the application head to the patient eye, for example to the cornea and/or sclera of the patient eye, is carried out by way of a patient interface, wherein the patient interface may comprise a transparent contact body, through which the laser pulses emerging from the projection lens are guided and which, by way of the mechanical contact with the cornea, fixes the latter in respect of the patient interface and the projection lens. As an alternative to coupling by means of a contact body, provision can be made of liquid coupling, wherein a coupling liquid, for example a physiological saline solution, is situated between the cornea and the projection lens. By way of example, corresponding patient interfaces are known from WO 2012031277. The patient interface can be coupled to the patient eye by means of a vacuum and a negative-pressure cavity of the patient interface. The negative-pressure cavity is typically a suction ring placed onto the cornea. Most suction rings have two sealing lips. The lips can be attached to the sclera, the sclera and the cornea, or only the cornea. Furthermore, there are variants which only have one ring and which generate a vacuum over the whole eye, or variants which consist of a plurality of suction chambers/suction cups. The suction ring is the most common method of fastening, but there are also other known solutions. In any case, coupling to the patient eye is carried out by a vacuum or a negative pressure in a negative-pressure cavity of the patient interface, wherein the negative-pressure cavity, along the circumference thereof, abuts on the patient eye in a sealing manner and thereby couples to the patient eye in a fluidically sealing manner and seals the latter from the surroundings. The negative pressure can be generated by a negative-pressure generator, in particular a vacuum pump or a negative-pressure pump. In the known systems, the patient interface is coupled to the application head by means of e.g. a screw-in connection, bayonet closures or vacuum couplings.

US 2002/0120285 A1 discloses a blade guidance for an ophthalmological surgical instrument, which is affixed on the patient eye by means of the vacuum and measures the contact pressure between the sclera and the blade guidance.

US 2002/0198553 A1 discloses a patient interface and a negative-pressure device with a fluidic pressure measurement, wherein the connection to the patient interface is carried out by way of a common fluidic line.

WO 2008/150330 discloses a patient interface which is provided for coupling to the patient eye by means of the vacuum and has a two-part design, wherein contact-pressure sensors are arranged at a coupling site between the parts, said sensors registering a contact pressure between the parts.

SUMMARY OF THE INVENTION

During the application, it is necessary to ensure, in particular, that the patient interface is connected to the patient eye in a secure and defined manner, and affixed on the latter. An insecure or detaching fixation would have as a consequence that the diagnostic or therapeutic beams emanating from the application head are no longer incident on the patient eye or—in a worst-case scenario—are incident on the patient eye in an undefined or incorrect manner.

By way of example, such a situation may occur if the line connecting the negative-pressure cavity of the patient interface with the negative-pressure generator is blocked. By way of example, this can arise by virtue of the air flow directed out of the negative-pressure cavity sucking in liquid, e.g. viscoelastics used in cataract operations, sterile covering film or binding tissue when establishing the negative pressure and thus wholly or partly blocking the negative-pressure connection line itself, serving for aspiration, and/or the connector thereof to the negative-pressure cavity, e.g. the interior of the suction ring. In this case, the negative-pressure generator cannot establish or maintain a negative pressure in the negative-pressure cavity of the patient interface that is sufficient for a secure fixation. Accordingly, a pressure measurement apparatus typically arranged at the end of the negative-pressure connection line, typically a pressure sensor, indicates a negative pressure in such a situation, even if sufficient negative pressure is not present in the negative-pressure cavity and the patient interface is not securely affixed to the patient eye or has even detached from the latter. A comparable situation arises if the negative-pressure connection line between negative-pressure generator and patient interface is bent over during operation. Such a state, in which there appears to be a sufficient negative pressure or a vacuum in the negative-pressure cavity, but it is not in fact present, is also referred to as a pseudo-vacuum.

A further typical source of error relates to the generation of temporary or permanent leakage between the negative-pressure cavity and patient eye or within the fluidic system, for example within the negative-pressure connection line itself or within the connector pieces thereof.

It is an object of the present invention to provide devices and methods which develop the prior art in respect of secure coupling between patient interface and patient eye and, in particular, improve the situation in respect of the detection of possible error states. In a general form, this object is achieved by the subject matter of the independent patent claims. Exemplary or advantageous embodiments are defined by the dependent patent claims and the whole disclosure of the present document.

In accordance with a first aspect, the object is achieved by provision of a negative-pressure device for affixing a patient interface on a patient eye. The negative-pressure device comprises a negative-pressure generator and a device-side negative-pressure interface for fluidic coupling of the negative-pressure generator to a negative-pressure cavity of the patient interface. The negative-pressure cavity is typically formed by the interior of the suction ring.

More specifically, affixing the patient interface on the patient eye means the affixment of a patient interface body on the patient eye, for example on the cornea and/or sclera. A side of the patient interface body lying opposite the patient eye is designed for coupling an ophthalmologic application head. The patient interface as a whole can comprise further components such as, in particular, connection lines.

The negative-pressure device furthermore comprises a fluidic pressure sensor, a device-side pressure sensor interface for coupling the pressure sensor to the patient interface in a manner functionally separate from the negative-pressure interface. Since pressure and force are related in a known way by way of the area, the pressure sensor can technically also be realized as a force sensor. The term "pressure sensor" should therefore also be read as "pressure-sensitive sensor" or "pressure-reactive sensor".

As a typically electric pressure sensor of a type known per se, the pressure sensor can be combined with further components of the negative-pressure device and, for example, be arranged in a common housing. In this case, the device-side pressure sensor interface is a fluidic interface. Furthermore, the pressure sensor can be spatially separate from further components of the negative-pressure device, in particular separate from the negative-pressure generator and/or the control apparatus. Then, the pressure sensor can be arranged e.g. directly at the patient interface body placed on the patient eye or it can be a component of a patient interface body. In the latter cases, the device-side sensor interface can be e.g. an electrical or fiber-optic interface. In principle, the negative-pressure device can consist of an individual compact instrument or a number of separate instruments or devices with corresponding operative coupling.

For operation, the pressure sensor is coupled to the patient interface in e.g. such a way that the negative pressure in the interior of the negative-pressure cavity acts on the pressure sensor and it is measured by the latter. In an alternative embodiment in accordance with the present disclosure, the pressure sensor can be a contact pressure sensor instead of a fluidic pressure sensor and it can be arranged in such a way that the contact pressure or the contact force between the patient interface, in particular the patient interface body, and the patient eye acts thereon and it measures said contact pressure or contact force. In any case, during operation, the pressure sensor measures a pressure or a force which has a functional relationship with the negative pressure in the interior of the negative-pressure cavity.

The negative-pressure device furthermore comprises a control unit operatively coupled to the negative-pressure generator and the pressure sensor or the device-side pressure sensor interface, wherein the control unit is designed to actuate the negative-pressure generator for the purposes of generating a negative pressure in the negative-pressure cavity. The control unit is furthermore designed to evaluate a pressure established by the pressure sensor.

In particular, evaluating the pressure can comprise establishing a faulty fluidic coupling of the negative-pressure-volume or consist of the latter. The faulty fluidic coupling can be a faulty fluidic coupling to the patient eye and/or a faulty fluidic coupling to the negative-pressure device or the negative-pressure generator thereof.

A faulty fluidic coupling of the negative-pressure cavity to the negative-pressure generator and/or the patient eye can emerge, in particular, from leakage/leaks and/or due to a pseudo-vacuum in accordance with the explanations above during the aspiration of the air from the negative-pressure-volume, or during running operation. The faulty fluidic coupling has as a consequence that the required negative pressure in the negative-pressure cavity is at least partly lost or cannot even be properly built up.

In the context of the present document, a "fluidic coupling" preferably means a geometrically defined fluidic coupling, for example by means of geometrically defined flow channels such as tubes, pipes and/or connection nozzles, and not a geometrically undefined fluidic coupling by way of the surrounding atmosphere. A "functionally separate coupling" means that the coupling is independent of the remaining fluidic system and there are no, or merely negligible, fluidic interactions. As presented in more detail below, this emerges, in particular, by means of a connection via separate flow channels, such as e.g. a separate fluidic connection line, and/or a direct integration of the pressure sensor into the patient interface body. The only fluidic coupling between the pressure sensor interface and the negative-pressure interface, and hence between the pressure sensor and the negative-pressure generator, is therefore brought about via the negative-pressure cavity of the patient interface.

In a fluidic context, a functionally separate coupling therefore causes a fluidically separate coupling. A functionally separate coupling of the pressure sensor to the negative-pressure cavity means, in particular, that there is no fluidic connection between the pressure sensor and the device-side pressure sensor interface on the one hand and remaining fluidic components of the negative-pressure device on the other hand, in particular the device-side negative-pressure interface and the negative-pressure generator. However, a mechanical integration, e.g. by way of a double connector with separate fluidic channels together with the negative-pressure interface, is not precluded.

Here, the functionally separate or functionally independent coupling extends on the whole fluidic path between the pressure sensor and the negative-pressure cavity. The flow channel connecting the pressure sensor with the negative-pressure cavity therefore leads from the pressure sensor to the negative-pressure cavity in a fluidically independent and preferably branch-free manner and opens directly into the negative-pressure cavity.

What is achieved by functionally separate coupling of the pressure sensor to the negative-pressure cavity is that the actual internal pressure of the negative-pressure cavity or a pressure correlated therewith acts on the pressure sensor—without the possible presence of further fault cases as discussed further below—even if the fluidic coupling by way of the negative-pressure interface is completely or partly blocked.

The negative-pressure generator typically comprises a vacuum type with a design known per se, but it can additionally or alternatively also comprise other suction or aspiration devices, in particular a negative-pressure reservoir in the form of a container to which negative pressure is applied. Optionally, the negative-pressure device comprises further fluidic components, such as one or more valves, some or all of which are operatively coupled to the control unit and can be controlled by the latter, chokes or positive-pressure valves.

The control unit is realized as an electronic circuit in a manner known per se and typically comprises one or more microprocessors and/or microcontrollers, memory components, other analog and/or digital semiconductor components, etc. Methods and algorithms for controlling the negative-pressure generator and for evaluating and processing the pressure sensor signal are typically realized wholly or in part in the form of program code for the at least one microprocessor and/or microcontroller, but can also be realized wholly or in part by corresponding circuit components.

The patient interface can be designed for coupling to the patient eye by means of coupling liquid and/or for applanation-type coupling by means of a transparent contact body. In the case of liquid coupling, the setpoint negative pressure $p_{nom}$, which is required for secure affixment of the patient interface and which should be built up and maintained by the negative-pressure device, lies in a typical range of −200 mbar . . . −850 mbar, for example, wherein a higher negative pressure is typically selected for coupling an applanation-type patient interface than for a patient interface with liquid coupling. In this document, negative pressures denote negative pressures in relation to ambient atmospheric pressure. In stationary operation after the negative pressure has been built up in the negative-pressure cavity, the control unit and the negative-pressure generator are typically designed to compensate pressure variations and maintain the setpoint negative pressure. The patient interface can be coupled to a therapeutic or diagnostic apparatus, for example a laser application head, before or after it is coupled to the patient eye.

The negative-pressure interface and the pressure sensor interface are typically designed as functionally detachable and nondestructive fluidic couplers, for example fluidic plug-in connectors. The patient interface can be coupled to a therapeutic or diagnostic apparatus, for example a laser application head, before or after it is coupled to the patient eye. In the case of a pressure sensor arranged outside of the negative-pressure device, the device-side pressure sensor interface however can also be or comprise a data interface, for example an electrical or optical interface. However, in principle, a secure coupling that is not detachable in a nondestructive manner with a patient interface is also possible.

In typical embodiments, the control unit is functionally coupled to an alarm device or designed for functional coupling to an alarm device. The control unit then is furthermore designed to activate the alarm device in the case of a detected faulty fluidic coupling of the negative-pressure cavity. The alarm device can be a component of the negative-pressure device and/or be external therefrom. The alarm device can typically comprise acoustic transducers such as loudspeakers, buzzers or sirens, in addition to optionally required actuation circuits such as warning lamps, light-emitting diodes etc., in addition to optionally present actuation circuits.

Furthermore, the control unit can be designed for operative wired and/or wireless coupling to a diagnostic and/or therapeutic radiation generator, in particular an ophthalmological laser device. The control unit can furthermore be configured to deactivate or switch off the radiation generator in the case of a detected faulty fluidic coupling of the negative-pressure cavity.

In one embodiment, the control unit is designed to detect a faulty fluidic coupling of the negative-pressure cavity by detecting a deviation between the pressure established by means of the pressure sensor and a reference pressure and/or by detecting a reduction in the negative pressure as a function of time.

Here, the reference pressure corresponds to a fixedly predetermined and/or adjustable, time-constant and/or time-variable setpoint negative pressure for securely affixing the patient interface. A faulty and/or insufficient affixment can be detected, in particular, by a continuous or virtually continuous comparison of the measured negative pressure with the setpoint negative pressure and/or by evaluating one or more characteristic values of a function formed by interpolating measurement values from the pressure sensor.

In one embodiment, the negative-pressure device comprises a second pressure sensor fluidically coupled to the device-side negative-pressure interface and operatively coupled to the control unit. Then, the control unit is designed to detect a faulty fluidic coupling of the negative-pressure cavity by means of a comparison of the established pressure with a second pressure established by the second pressure sensor.

A second pressure sensor can be fluidically coupled to, in particular, the negative-pressure interface and the negative-pressure generator and it can be arranged, for example, in or at one end of a fluidic connection line between negative-pressure coupler and negative-pressure generator or optionally interposed valves. In the case of a correct and continuous fluid connection between the negative-pressure cavity and the negative-pressure device, the pressures measured by the pressure sensor and the second pressure sensor correspond to one another, at least during stationary operation. A deviation between the measured pressures going beyond measurement uncertainty is an indication of a faulty coupling, in particular due to a pseudo-vacuum or a leakage. The control unit can furthermore be designed to establish a technical error of one of the pressure sensors, the fluidic and electric coupling thereof and/or downstream electronic components by way of a comparison between the established pressures, as presented in more detail in the context of exemplary embodiments. Since the pressure sensor and the second pressure sensor are redundant to one another, at least in stationary operation, a complete or partial blockage or a leak of the fluidic coupling of the pressure sensor can furthermore be detected by means of the optional second pressure sensor.

During stationary operation of the negative-pressure device, the pressure sensor, for example, can serve for monitoring while closed-loop control of the negative-pressure generator for the build up or controlled maintenance of negative pressure in the negative-pressure cavity is carried out using a control loop including the second pressure sensor. However, it is likewise possible to use the pressure sensor for closed-loop control.

In one embodiment, the negative-pressure device comprises a flow sensor fluidically coupled to the device-side negative-pressure interface and operatively coupled to the control unit. By way of example, the flow sensor can be a volume flow sensor or a mass flow sensor.

In this embodiment, the control device is additionally designed to evaluate the flow established by the flow sensor. Further aspects and embodiments including a flow sensor are discussed in the context of exemplary embodiments.

In one embodiment, the negative-pressure device comprises a valve unit fluidically coupled to the device-side negative-pressure interface and the negative-pressure generator and operatively coupled to the control unit. In an embodiment with a valve unit, the valve unit is designed to alternatively fluidically seal the device-side negative-pressure interface, fluidically couple the latter to the negative-pressure generator or fluidically couple said device-side negative-pressure interface with an equalization volume.

A valve unit can serve, in particular, for switching between different modes of operation or operating states of the negative-pressure device, for example for switching between an aspiration operation for building up negative pressure in the negative-pressure cavity, a holding operation or stationary operation for maintaining the desired negative pressure, and a ventilation operation, in which the negative-pressure cavity is ventilated in respect to the surroundings and the affixment of the patient interface on the patient eye is lifted. Furthermore, ventilating the negative-pressure cavity is reliably detectable by means of the pressure sensor coupled in a functionally separate manner. In this way, the presence of error states in the ventilation operation, such as faulty valve couplings or bent-over tubes etc., is detectable. The control unit can optionally be designed for detecting such further error states.

The valve unit can comprise one or more valves realized individually or integrally and it can be provided for a separate or common actuation of valves by way of the control unit.

In one embodiment, the negative-pressure device comprises a patient interface coupler which comprises both the device-side negative-pressure interface and the device-side pressure sensor interface. The patient interface coupler is typically equipped as a detachable and nondestructively re-connectable fluidic plug-in connector or fluidic coupling sleeve with separate fluidic channels for the device-side negative-pressure interface and for the device-side pressure sensor interface.

In accordance with a further aspect, the object is achieved by the provision of a patient interface. The patient interface is designed for coupling to a patient eye. The patient interface comprises a negative-pressure cavity designed for fluidic coupling to the patient eye. The patient interface furthermore comprises an interface-side negative-pressure interface fluidically coupled to the negative-pressure cavity, for fluidically coupling the negative-pressure cavity to a negative-pressure generator. The patient interface furthermore comprises an interface-side sensor interface fluidically coupled to the negative-pressure cavity, for fluidically coupling the negative-pressure cavity to a fluidic pressure sensor. Here, the interface-side sensor interface is functionally, in particular fluidically, separate from the interface-side negative-pressure interface. The fluidic coupling of the negative-pressure cavity to the pressure sensor means that, during operation, the pressure in the interior of the negative-pressure cavity acts on the pressure sensor and it is measured by the latter.

The explanations made above apply in respect of the functionally separate coupling between the pressure sensor, on the one hand, and the negative-pressure cavity, on the other hand. The functionally and hence in particular fluidically separate coupling of the pressure sensor extends over the whole fluidic path between the pressure sensor and the interface-side sensor interface. The interface-side sensor interface is situated in, or opens directly into, the negative-pressure cavity. Here, the pressure sensor coupled to the patient interface during operation is a fluidic pressure sensor, as described above.

The patient interface can be designed for coupling to the patient eye by means of a coupling liquid and/or for e.g. an applanation-type coupling by means of a transparent contact body.

Apart from the interface-side sensor interface provided separately from the interface-side negative-pressure interface, the patient interface can be embodied in a design known per se and in a single part or multipart manner. By way of example, the negative-pressure cavity is formed as a suction ring by a chamber which is open toward the patient eye and encircles the latter in a ring-shaped manner.

Exemplary multipart patient interfaces have a design in accordance with US20150088103A1 and EP2853247A1 which, in respect of the design of exemplary patient interfaces, are incorporated into the present document, also for exemplary embodiments described in more detail below. However, the specific structure of the patient interface is not mandatory.

Typically, the patient interface is configured as a disposable product for economic reasons and as a result of safety considerations and it is preferably packaged in a sterile manner at first. However, in principle, the patient interface can also be designed entirely in parts for multiple use.

In one embodiment, the patient interface comprises a negative-pressure connection line and a pressure sensor connection line functionally separate from the negative-pressure connection line. That part of the patient interface, which is provided for affixment on the patient interface and which comprises the negative-pressure cavity, from which the negative-pressure connection line and the pressure sensor connection line emanate.

The negative-pressure connection line and the pressure sensor connection line are typically configured as plastic tubes which are pressure resistant to the required extent and flexible and fluidically not connected. Typically, they are securely fluidically coupled, in a manner known per se, to the negative-pressure cavity at the end thereof facing the patient interface body, for example by way of separate conical connection pieces of the patient interface body. Furthermore, the connection lines can be cohesively connected to the patient interface body, for example by adhesive bonding or welding. However, alternatively, detachable fluidic plug-in connectors can also be provided at the patient interface body for a detachable connection to a separate negative-pressure connection line or pressure sensor connection line.

In one embodiment, the patient interface comprises a negative-pressure device coupler which comprises both the interface-side negative-pressure interface and the interface-side pressure sensor interface. In these embodiments for coupling to a patient interface coupler of a negative-pressure device, the negative-pressure device coupler can be designed as a counter piece. While the handling during operation is simplified by the mechanical integration, the fluidically separate coupling remains untouched therefrom.

However, as an alternative to a coupler comprising both the interface-side negative-pressure interface and the interface-side pressure sensor interface, provision can also be made of separate fluidic couplers, for example separate fluidic plug-in connectors.

Furthermore, the pressure sensor interface can also be designed for direct coupling of the pressure sensor without the fluidic pressure sensor connection line, which coupling is preferably nondestructively detachable, at least for the pressure sensor. In such an embodiment, the pressure sensor is coupled directly to the patient interface or the patient interface body and the functional coupling to further elements of the negative-pressure device, in particular the control unit, is established by way of a communication interface, e.g. an electric line which in this case replaces the pressure sensor connection line. Here, the pressure sensor interface is integrated directly into the negative-pressure cavity, for example in an outer wall of the negative-pressure cavity, or it opens into the latter.

In one embodiment, the patient interface comprises a liquid collector, in particular a drip chamber, arranged fluidically between the negative-pressure cavity and the interface-side negative-pressure interface. A drip chamber arranged thus is known per se from the prior art and, in the case of a patient interface according to the disclosure, it keeps back liquid aspirated from the negative-pressure cavity together with the air. What this prevents is that said liquid comes into contact with the fluidic system downstream thereof, in particular with the negative-pressure generator, the pressure sensor and possible valves. In typical embodiments, these components are not designed for a liquid contact and can be damaged thereby and, for example, measurement values from the pressure sensor can be falsified as a result of this.

In accordance with a further aspect, the object is achieved by the provision of a further patient interface for affixment on a patient eye. This patient interface comprises a negative-pressure cavity designed for fluidic coupling to the patient eye. The patient interface furthermore comprises an interface-side negative-pressure interface fluidically coupled to the negative-pressure cavity, for fluidically coupling the negative-pressure cavity to a negative-pressure generator. The patient interface furthermore comprises a fluidic pressure sensor. The pressure sensor is fluidically coupled to the negative-pressure cavity in a manner functionally separate from the interface-side negative-pressure interface or designed to determine a contact pressure between patient interface and patient eye. The pressure sensor can be a (miniaturized) electronic pressure sensor or pressure transducer of a manner known per se, for example on a piezoresistive basis. The explanations made above apply in respect of the functionally separate coupling of the pressure sensor to the negative-pressure cavity.

For this type of patient interface, a pressure sensor is integrated immediately into the patient interface or the patient interface body. An electrical or optical connection line, present here for coupling the pressure sensor to the negative-pressure device, is typically less susceptible to interruptions, bending over, etc.

In addition or as an alternative to an operative connection to the negative-pressure device and, in particular, to the control unit thereof, as described above, the pressure sensor can also be designed for an operative coupling to a separate evaluation device, wherein the evaluation device is designed to evaluate a pressure established by the pressure sensor. Functions of the evaluation device in this respect can correspond to functions explained in the context of the control unit of a negative-pressure device. By way of example, for autonomous operation, an evaluation device can also be coupled directly structurally to the patient interface body and/or integrated in the latter. The evaluation device can comprise display elements and/or alarm apparatuses, for example in the form of analog and/or digital displays, light-emitting diodes, acoustic signal transducers etc., which are configured to indicate an error state, for example a faulty coupling of the patient interface.

According to the disclosure, as an alternative or in addition to measuring the pressure or negative pressure in the interior volume of the negative-pressure cavity, the pressure sensor can also be designed as a contact pressure sensor for establishing the contact pressure or contact force between the patient interface body and patient eye. In such embodiments, a measurement surface, provided for the pressure to be measured or the force to be measured to act thereon, of the pressure sensor is designed for contact with the patient eye. This embodiment is particularly expedient for detecting a faulty or insufficient coupling of the patient interface to the patient eye, for example due to a leakage. In this case, the pressure sensor is a contact pressure sensor.

In one embodiment of a patient interface with a pressure sensor, the pressure sensor comprises an optical indicator element. It varies the optical properties thereof in a manner dependent on the pressure acting on the optical indicator element.

The optical indicator element in such an embodiment can be e.g. a tension-optical element which, in the case of a mechanical load in conjunction with a polarized light source, exhibits a colored pattern reflecting the mechanical load, in particular the mechanical tension. Such an optical indicator element, for example in the form of a flexure beam coupled to the interior of the negative-pressure cavity, can be integrated into a wall of the negative-pressure cavity, for example into a suction ring wall. In such an embodiment, a pressure sensor or optical indicator optically accessible to the surgeon allows a manual assessment of the pressure in the negative-pressure cavity, even without additional electronic apparatuses. Optionally, the pressure sensor can also comprise an electronic sensor, for example a miniaturized camera unit, photodiode, etc., which is optically coupled to the optical indicator element and which registers the pressure-dependent change in the optical properties. Furthermore, the optical indicator unit can be connected to an optical pressure sensor connection line by way of an optical conductor, e.g. one or more optical fibers.

In accordance with a further aspect, the object is achieved by the provision of a method for coupling a patient interface to a patient eye. The method comprises building up negative pressure in a negative-pressure cavity of the patient interface by means of a negative-pressure generator coupled fluidically to the negative-pressure cavity. The method furthermore comprises establishing a pressure in the negative-pressure cavity by means of a pressure sensor coupled to the patient interface in a manner functionally separate from the negative-pressure generator. The method furthermore comprises evaluating the pressure established by means of the pressure sensor. Evaluating the pressure can describe, in particular, the detection of a faulty fluidic coupling of the patient interface as described above and below in the context of exemplary embodiments.

In one embodiment, the detection of a faulty fluidic coupling of the negative-pressure cavity comprises a detection of a deviation between the pressure established by means of the pressure sensor and a reference pressure and/or a detection of a reduction in the negative pressure as a function of time.

In one embodiment, the detection of a faulty fluidic coupling of the negative-pressure cavity comprises a comparison of the pressure established by means of the pressure sensor with a second pressure established by means of a second pressure sensor. Here, the second pressure sensor is coupled to the negative-pressure cavity in a manner functionally separate from the pressure sensor.

Methods according to the invention can be carried out, in particular, by or using disclosed negative-pressure devices and patient interfaces. Therefore, disclosed exemplary embodiments of negative-pressure devices and/or patient interfaces should simultaneously be understood to be a disclosure of corresponding embodiments of the method, and vice versa.

In accordance with a further aspect, the object is achieved by a computer program product. The computer program product comprises a non-transient computer-readable medium with computer program code stored thereon. The program code is configured to control one or more processors of a negative-pressure device in such a way that a control unit of the negative-pressure device actuates a negative-pressure generator of the negative-pressure device for building up a negative pressure in a negative-pressure cavity of a patient interface fluidically coupled to the negative-pressure generator;

the control unit establishes a pressure in the negative-pressure cavity by means of a fluidic pressure sensor coupled to the negative-pressure cavity in a functionally separate manner from the negative-pressure generator;

the control unit evaluates the pressure established by means of the pressure sensor, in particular detects a faulty fluidic coupling of the patient interface.

The one or more processors can in particular be one or more microprocessors and/or microcontrollers of the control unit. The computer program code can be configured, in particular, to control one or more processors for executing one or more of the disclosed methods.

In accordance with a further aspect, the object is achieved by the provision of an ophthalmological arrangement. The ophthalmological arrangement comprises a negative-pressure device and a patient interface in accordance with an embodiment disclosed above and/or below in the context of examples.

EXEMPLARY EMBODIMENTS

Exemplary embodiments are presented below with additional reference to the figures.

Figure 1:
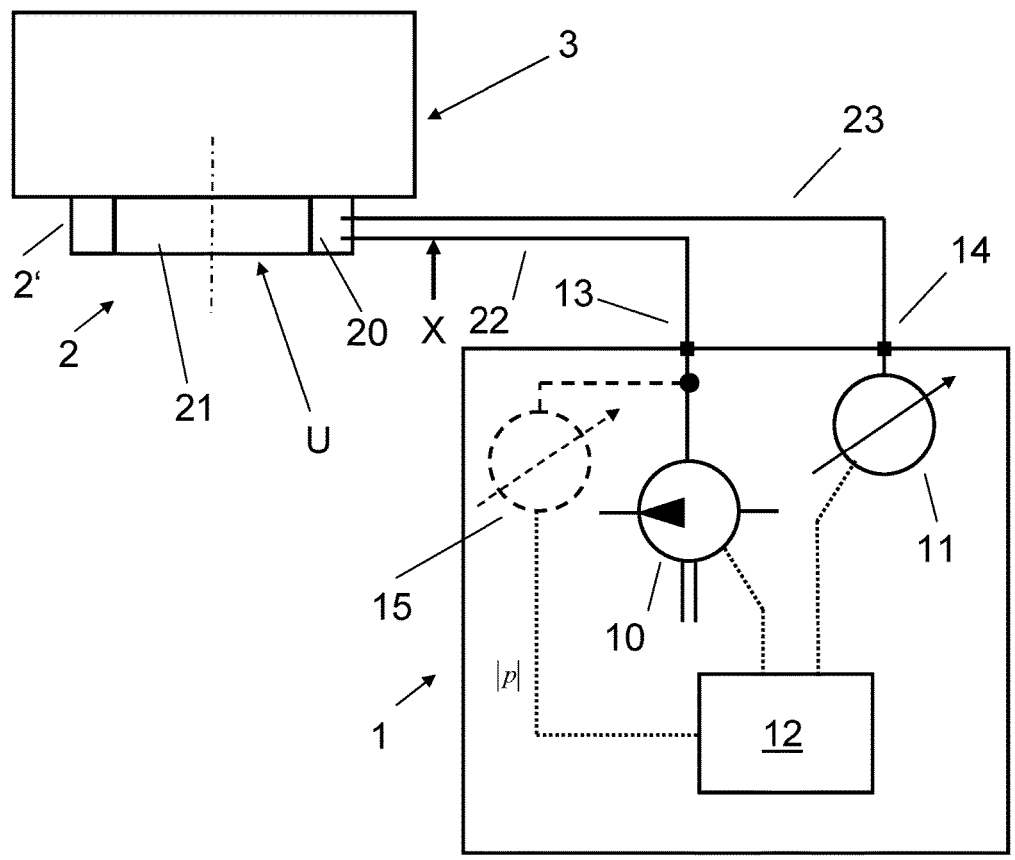
FIG. 1 schematically shows an embodiment of an ophthalmological arrangement of negative-pressure device and a patient interface.

In FIG. 1, the reference sign 1 denotes a negative-pressure device and the reference sign 2 denotes a patient interface connected to the negative-pressure device 1 in a schematic cross-section. The patient interface 2 is coupled to an ophthalmological application head 3. Together, the negative-pressure device 1 and the patient interface 2 form an ophthalmological arrangement according to the invention.

In the application state, the patient interface 2 abuts with its lower side U of the patient interface body 2' on the cornea of the patient eye (not depicted here). The patient interface body 2' of the patient interface 2 has e.g. a cylindrical interior 21, which is situated between the corneal surface of the patient eye and the application head 3 in the application state and which can be filled with e.g. physiological saline as a coupling liquid. A suction ring is arranged concentrically around the interior 21, said suction ring likewise abutting on the cornea of the patient eye in the application state and the interior thereof forming a ring-shaped negative-pressure cavity 20. For the purposes of coupling the patient interface 2 or the patient interface body 2' to the patient eye, a negative pressure or vacuum is generated in the negative-pressure cavity 20 and a negative pressure or vacuum thus fixes the patient interface 2 on the patient eye.

The negative-pressure device 1 comprises a negative-pressure generator 10, which is typically formed by a vacuum pump. The negative-pressure device 1 furthermore comprises a fluidic pressure sensor 11 and a control unit 12 operatively connected to the negative-pressure generator 10 and the pressure sensor 11, said control unit typically being formed by an electric/electronic circuit in a manner known per se. In particular, the control unit 12 can comprise one or more microprocessors and/or microcontrollers with appropriate program code for controlling the function of the negative-pressure device 1. The control unit 12 comprises an alarm device or it is operatively coupled to an alarm device (not depicted here). An alarm is sounded by way of the e.g. optical and/or acoustic alarm device in the case of a determined fluidic coupling. The control unit 12 can furthermore be operatively coupled to a ophthalmological laser light source connected to the application head 3 or contained in the application head 3 or operatively coupled to any other beam generator and it can deactivate or switch off said ophthalmological laser light source or other beam generator in the case of a detected faulty fluidic coupling of the negative-pressure cavity.

The negative-pressure device 1 furthermore comprises a device-side negative-pressure interface 13 and a device-side pressure sensor interface 14, which are formed, for example, by detachable fluidic plug-in connectors or couplers, e.g. fluidic coupling sleeves. Here, the device-side negative-pressure interface 13 is fluidically coupled to the negative-pressure generator 10 and the device-side pressure sensor interface 14 is separately fluidically coupled to the pressure sensor 11.

The patient interface 2 furthermore comprises a negative-pressure connection line 22 and a pressure sensor connection line 23 which is fluidically separate from the negative-pressure connection line 22. At one end, the negative-pressure connection line 22 and the pressure sensor connection line 23 are fluidically coupled, in each case separately, to the negative-pressure cavity 20, wherein the fluidically separate coupling in each case extends on the whole fluidic path and, in particular, as far as the negative-pressure cavity 20. At the respective other end, the negative-pressure connection line 22 and the pressure sensor connection line 23 each have a fluidic coupling element (not depicted separately here), e.g. a fluidic plug-in connector, which is provided for a detachable coupling to the device-side negative-pressure interface 13 and the device-side pressure sensor interface 14, respectively.

For the purposes of coupling the patient interface 2 onto the patient eye, the negative-pressure generator 10 is actuated or put into operation by the control unit 12 such that the air originally present in the negative-pressure cavity 20 is at least partly aspirated. The pressure sensor 11 coupled in a functionally separate manner to the negative-pressure cavity 20 measures the effective pressure present in the negative-pressure cavity 20 in a manner independent of the negative-pressure connection line 22.

Figure 2:
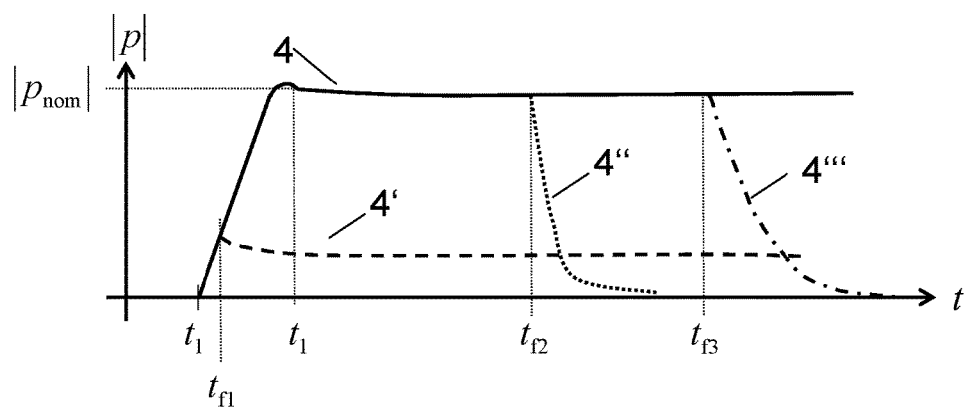
FIG. 2 schematically shows various pressure curves as a function of time.

Below, reference is additionally made to FIG. 2. In the curve denoted by the reference sign 4, FIG. 2 illustrates the magnitude of the negative pressure p, as measured by the pressure sensor 11, as a function of time t for a correct affixment of the patient interface 2 on the patient eye. Here, a value of p=0 corresponds to ambient pressure and an increasing negative pressure (decreasing absolute pressure) corresponds to an increasing curve profile.

In the aspiration phase starting at the time $t_0$, air present in the negative-pressure cavity 20 is aspirated by the negative-pressure generator 10 through the negative-pressure connection line 22, as a result of which there is an increase in negative pressure. At a setpoint negative pressure of e.g. $p_{nom}$=−400 mbar, corresponding to the envisaged operating state, the control unit 12 switches at the time $t_1$ in a manner known per se into a stationary holding operation, in which the negative pressure in the negative-pressure cavity 20 is kept substantially constant. This state is maintained until a pressure equalization with the surroundings is established deliberately and the patient interface 2 is thus detached from the cornea of the patient eye.

The air flow arising from the negative-pressure-volume in the direction of the negative-pressure device 1 or the negative-pressure generator 10 when aspirating the air from the negative-pressure-volume 20 moreover brings about a removal of possibly present liquid droplets, remains of sterile covering film, etc. from the region of the coupling between the pressure sensor connection line 23 and negative-pressure-volume 20.

The curve 4' in FIG. 2 schematically shows the pressure p measured by the pressure sensor 11 if a pseudo-vacuum as described in the general description arises at a first fault time $t_{f1}$, for example as a result of the negative-pressure connection line 22 bending over during the aspiration process at a point marked by "X" in an exemplary manner in FIG. 1. A pressure sensor 15 connected in the negative-pressure device 1 to the negative-pressure connection line 22, as is typically present in the prior art and as is optional in the device shown in FIG. 1, cannot detect the bending of the negative-pressure connection line 22 since negative pressure still is present or still is being built up further between the location of the bending and the negative-pressure device 1 or the negative-pressure generator 10, and therefore the pressure sensor 15 measures a negative pressure which, however, is not present in the negative-pressure cavity 20.

By contrast, the pressure sensor 11 measures the pressure effectively present in the negative-pressure cavity 20 due to the direct coupling of the pressure sensor 11 to the negative-pressure cavity 20, which coupling is independent of the negative-pressure connection line 22. Accordingly, the negative pressure measured by the pressure sensor 11 no longer increases after the negative-pressure connection line 20 bends over, even though the negative-pressure generator 10 continues to operate. The negative pressure in the negative-pressure cavity 20 remains substantially constant (on a level that is too low) after the occurrence of the pseudo-vacuum or it drops again due to elasticity and/or leakage possibly present, and so there is pressure equalization with the surroundings.

The curve 4" in FIG. 2 represents the pressure measured by the pressure sensor 11 in the case where the negative pressure in the negative-pressure cavity 20 is reduced at a second error time $t_{f2}$ (after an initial build up of the negative pressure which was carried out correctly and after the correct affixment of the patient interface 2 on the patient eye) during the stationary operation. By way of example, this is the case if the patient interface 2 briefly and partially detaches from the patient eye, which, in the most inexpedient cases, may occur due to a necessary movement of the patient interface by the ophthalmologist or else by a movement of the patient himself. In this case, there is an at least partial pressure equalization with the surroundings and hence a reduction of the negative pressure in the negative-pressure cavity 20. In principle, this reduction in pressure can be detected by the pressure sensor 15 and the negative-pressure generator 10 can reestablish the correct negative pressure, at least in the case of only brief leakage. However, if the negative-pressure connection line 22 itself is bent over or unpassable for another reason, the reduction in the negative pressure is not identified by the pressure sensor 15. In the case of an only partly passable negative-pressure connection line 22, there is at least an increase in the control delay when compensating the reduction in pressure such that secure affixment of the patient interface 2 on the patient eye is possibly no longer given or at least cannot be ensured. The pressure sensor 11 connected directly to the negative-pressure cavity 20 according to the invention correctly determines the reduction in the negative pressure in accordance with curve 4".

The curve 4''' in FIG. 2 represents the case where the negative pressure reduces slowly (compared to the profile depicted in curve 4") at a third error time $t_{f3}$ (after an initial build up of the negative pressure which was carried out correctly and after the correct affixment of the patient interface 2 on the patient eye), which may be caused by e.g. slight leakage or a leak of a fluidic connector.

Determining error states in respect of the affixment of the patient interface 2 on the patient eye by evaluating the pressure measured by the pressure sensor 11 or the electrical signal corresponding to the pressure can be carried out alternatively by the control device 12 or, in a complementary manner, according to different methods, which are typically carried out by one or more microcontrollers and/or processors of the control device 12 with corresponding program code/firmware. However, one or more methods can also be realized wholly or in part by special hardware and corresponding circuits.

According to one method, the pressure measured by the pressure sensor 11 is compared continuously or virtually continuously to at least one limit negative pressure $p_{limit}$. This limit pressure $p_{limit}$ typically lies lower in terms of magnitude than the setpoint negative pressure $p_{nom}$ and can, for example, be represented by the magnitude of the setpoint negative pressure $p_{nom}$ from which a safety value determined by tolerances, measurement uncertainties, etc. was subtracted. In the aspiration phase, the limit pressure $p_{limit}$ can be adapted continuously in accordance with the pressure profile emerging during correct operation. An error case then is assumed if the limit pressure $p_{limit}$ is undershot.

According to a further alternative or complementary method, the pressure measured by the pressure sensor 11 is evaluated continuously or virtually continuously in respect of a drop or reduction in the negative pressure. To this end, use can be made of several methods from signal processing and/or statistics, known per se, for example the determination and evaluation of the gradient and/or further characteristic values of a function formed by an interpolation of measurement values.

If the negative-pressure device 1 additionally comprises the optional second pressure sensor 15, detecting a faulty or insufficient affixment can be carried out using a comparison or combined evaluation of the pressures established by the pressure sensor 11 and the second pressure sensor 15 in accordance with a further alternative or complementary method. In the case of correct coupling of the patient interface 2 and without the presence of an error state, the pressures measured by the pressure sensor 11 and the second pressure sensor 15 are substantially equal, at least in the stationary operating state, and the sensors 11, 15 are therefore redundant. Accordingly, detecting a faulty or insufficient fluidic coupling of the patient interface can comprise detecting of a deviation between the pressures established by the pressure sensor 11 and the second pressure sensor 15. Here, establishing the deviation can be carried out by means of methods from signal processing and/or statistics, known per se, and can comprise e.g. establishing and evaluating the difference between the established pressures and comparing this with an admissible maximum difference, which is typically determined from tolerances and measurement uncertainties. As an alternative or in a complementary manner to the formation of a difference, determining a faulty or insufficient coupling can e.g. comprise establishing and evaluating a correlation of the pressures established by the pressure sensor 11 and the second pressure sensor 15 as a function of time t.

It should be noted in the case of a common evaluation of the pressures established by the pressure sensor 11 and the second pressure sensor 15 that the pressure sensor 11, particularly when building up the negative pressure in the negative-pressure cavity 20 and when ventilating, reacts more quickly to pressure changes in the negative-pressure cavity 20 than the second negative-pressure sensor 15. This emerges from the fact that there simultaneously is a displacement of an air volume through the negative-pressure connection line 22, while the pressure sensor connection line 23 is fluidically sealed by the pressure sensor 11.

The control device 12 can furthermore be configured to apply various methods for detecting a faulty and/or insufficient fixation in parallel or alternatively.

By a common evaluation of the pressures established by the pressure sensor 11 and the second pressure sensor 15, the control device 12 is able furthermore to detect further error states, for example a pseudo vacuum of the pressure sensor connection line 23 and/or a defect of either the pressure sensor 11 or the second pressure sensor 15, of the electrical contacting thereof or of downstream components.

Figure 3:
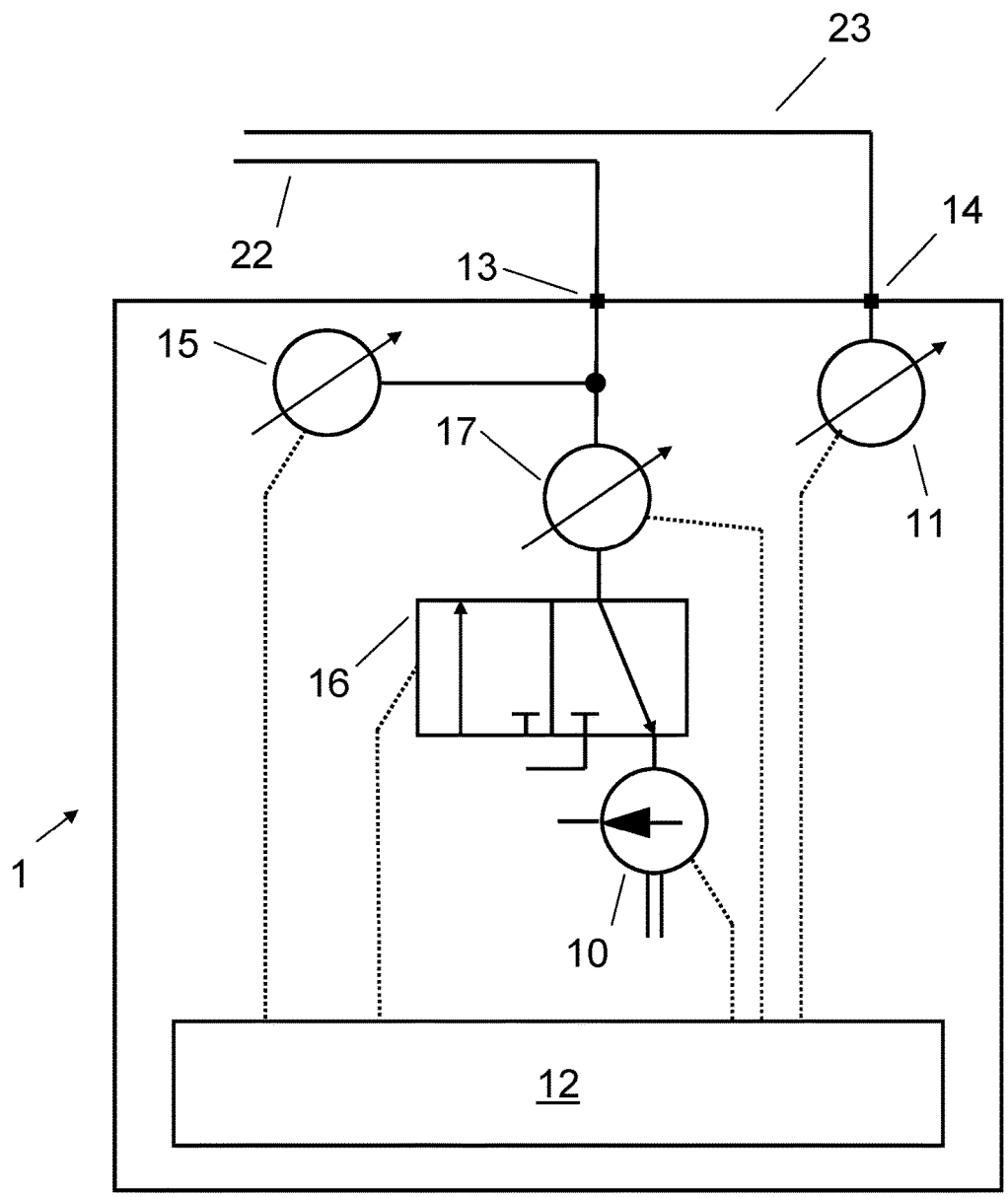
FIG. 3 schematically shows a further embodiment of a negative-pressure device.

Below, reference is additionally made to FIG. 3. FIG. 3 shows a further exemplary embodiment of the negative-pressure device 1. The negative-pressure device 1 from FIG. 3, in principle, has a similar design to the negative-pressure device 1 in accordance with FIG. 1, but it additionally contains a valve unit 16 which is operatively coupled to the control unit and actuated by the control unit 12.

By way of the valve unit 16, the negative-pressure supply line 22 is alternatively connected to the negative-pressure generator 10 (depicted position) for building up and maintaining the negative pressure or it is connected to the surroundings for ventilating and reducing the negative pressure in the negative-pressure cavity 20.

The embodiment of the negative-pressure device 1 depicted in FIG. 3 furthermore comprises an optional flow sensor 17, which is fluidically arranged between the device-side negative-pressure interface 13 and the valve unit. The flow sensor 17 serves to detect error states, in particular temporary or permanent leaks, which cause an increased airflow when aspirating air from the negative-pressure cavity 20. Furthermore, while the presence of the pseudo vacuum in accordance with the manner described above causes the second pressure sensor 15 to measure negative pressure when operating the negative-pressure generator 10, there is no, or only a reduced, airflow through the flow sensor 17 compared to the situation without a pseudo vacuum.

The embodiments of a negative-pressure device 1 depicted in FIG. 1 and FIG. 3 can be modified in various ways. For example, instead of being arranged within a housing (not provided with a reference sign) of the control unit 12, the pressure sensor 11 can be arranged directly on or in the patient interface 2, wherein the pressure sensor connection line 23 is dispensed with and, instead, provision is made of an electric pressure sensor connection line. By way of example, in such embodiments, the pressure sensor 11 can be a miniaturized disposable pressure sensor which, for example, is securely assembled with the patient interface body 2', or the patient interface body 2', or the negative-pressure cavity 20, and the pressure sensor 11 have a fluidic interface which is at least nondestructively detachable for the pressure sensor 11.

The device-side negative-pressure interface 13 and the device-side pressure sensor interface 14 can also be situated at the interface to the patient interface body 2' instead of being situated at a housing of the negative-pressure device 1. In this case, the negative-pressure connection line 22 and the pressure sensor connection line 23 can be wholly or partly part of the negative-pressure apparatus 1. The fluidic interfaces 13, 14 can be realized by means of separate fluidic couplers, for example separate fluidic plug-in connectors, or they can be integrated in a common fluidic coupler or plug-in connector.

The design, in particular the fluidic design, of the negative-pressure device 1 can be modified further and, in particular, comprise further components. For example, the valve arrangement 16 in accordance with FIG. 3 can comprise further valves and enable further fluidic configurations. Thus, for example, provision can be made for the negative-pressure generator 10 to be connected fluidically to the surroundings. Furthermore, provision can be made for the negative-pressure connection line 22 to be fluidically sealed or fluidically isolated together with the connected second pressure sensor 15. Furthermore, a negative-pressure reservoir with a volume of the order of e.g. one liter can be provided, said negative-pressure reservoir being connectable to the negative-pressure supply line 22 and/or the negative-pressure generator 10 by means of the valve arrangement. In particular, such a negative-pressure reservoir serves for fluidic buffering and can furthermore serve for aspirating small amounts of air, for example in the case of a relatively small and short-lived leakage of the negative-pressure cavity 20, in place of, and with in principle the same function as, the negative-pressure generator. Advantageously, a negative pressure is built up in the optional negative-pressure reservoir by means of the negative-pressure generator 10.

Figure 4:
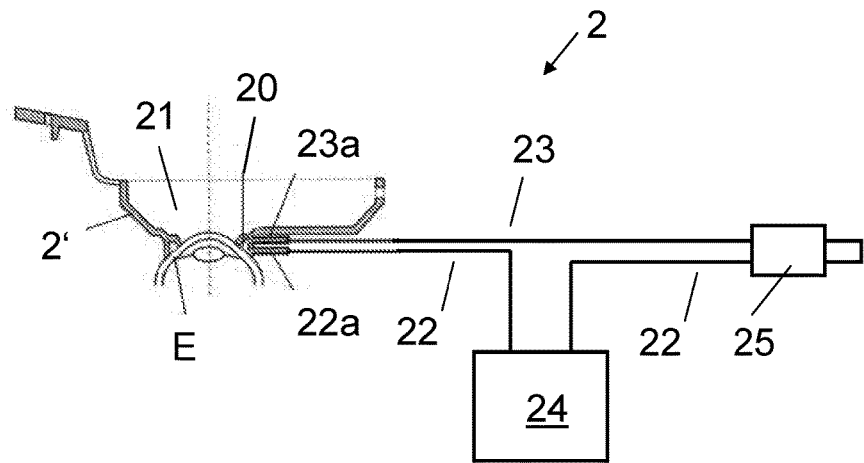
FIG. 4 schematically shows an embodiment of a patient interface.

Below, reference is additionally made to FIG. 4. FIG. 4 schematically depicts part of a patient interface 2 in accordance with an exemplary embodiment of the invention together with a patient eye E. The patient interface 2 has a patient interface body 2' with a ring-shaped negative-pressure cavity 20 and an interior 21. Two fluidic connection nozzles 22a, 23a, which are connected to the patient interface-side ends of the negative pressure supply line 22 and the pressure sensor connection line 23 in a fluidically tight manner known per se, e.g. by adhesive bonding, ultrasonic welding or friction, open separately into the negative-pressure cavity. The device-side ends of the fluidic lines 22, 23 open into a common negative-pressure device coupler 25 in the form of a plug-in connector, which, during operation, is coupled to a corresponding patient interface coupler of the negative-pressure device 1 in the form of a fluidic coupling sleeve. The negative-pressure device coupler 25 and the associated patient interface coupler are double connectors, which are designed for the common establishment or dissolution of two fluidically separate connections. Even though such a double connector is advantageous in view of operational safety and handling, provision can alternatively also be made of two separate couplers, e.g. simple fluidic plug-in connectors.

The patient interface 2 in accordance with FIG. 4 furthermore comprises a drip chamber 24 optionally seated in the negative-pressure connection line 22. The drip chamber separates liquid aspirated from the negative-pressure cavity 20, e.g. drops of physiological saline as a coupling liquid, and thus prevents these from reaching the fluidic components of the negative-pressure device 1 during operation.

Since the drip chamber 24 is arranged fluidically between the negative-pressure cavity 20 and the second pressure sensor 15, it retards the response of the second pressure sensor 15 or increases the inertia thereof. However, this does not apply to the pressure sensor 11 directly coupled to the negative-pressure volume 20, and so said pressure sensor reacts more quickly to pressure changes in the negative-pressure volume 20.

Figure 5:
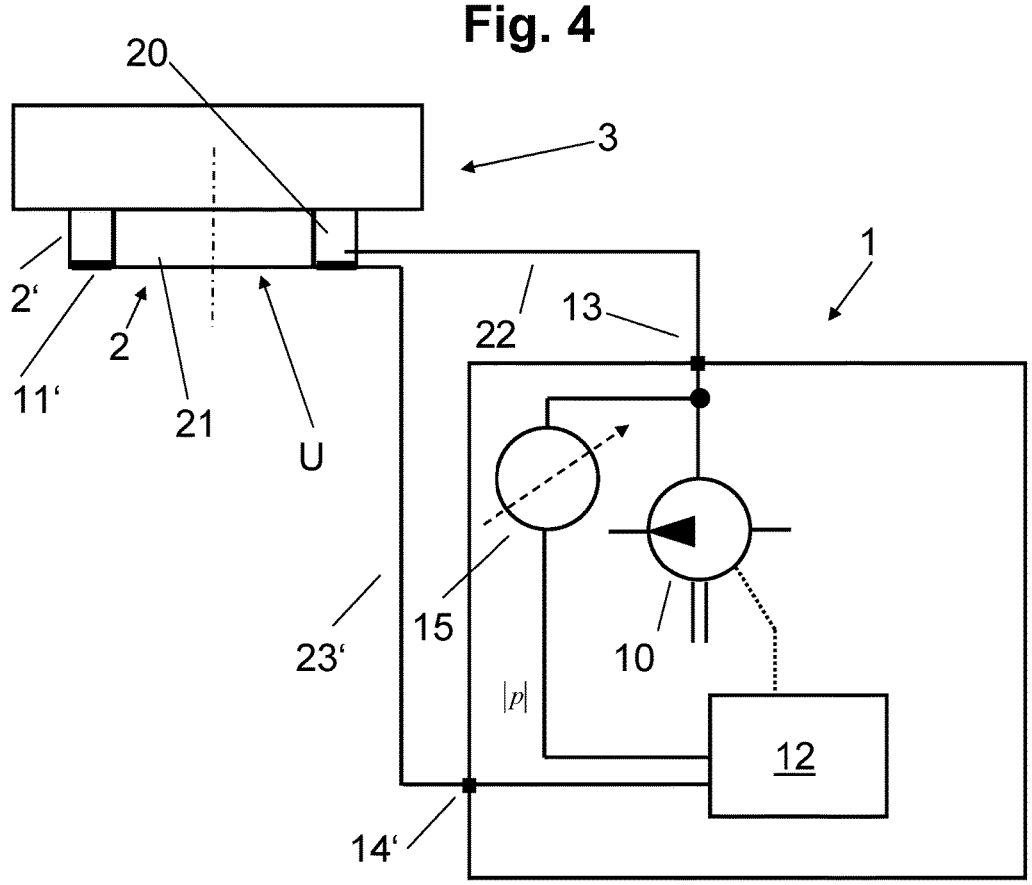
FIG. 5 schematically shows a further embodiment of an ophthalmological arrangement.

Below, reference is additionally made to FIG. 5. FIG. 5 depicts a further embodiment of an ophthalmological arrangement with a further embodiment of the negative-pressure device 1 and a further embodiment of the patient interface 2 in a schematic functional illustration and in an operatively coupled state. To the extent that nothing is mentioned below, the negative-pressure device 1 and the patient interface 2 according to FIG. 5 can have an analogous design to the illustration in accordance with FIG. 1 and have a corresponding functionality.

In the embodiment in accordance with FIG. 5, the fluidic pressure sensor 11 has been replaced by a contact pressure sensor 11', which is arranged in the patient interface 2. The contact pressure sensor 11' is designed to measure the contact pressure between patient interface 2 and the patient eye and it is integrated, for example in a ring-shaped manner, in the side of a wall of the suction ring facing the patient eye. Alternatively, provision can also be made of a plurality of isolated contact pressure sensors along the circumference of the suction ring, or else of only a single isolated contact pressure sensor.

In this form, the fluidic pressure sensor connection line 23 of FIG. 1 has been replaced by an electrical pressure sensor connection line 23', by means of which the contact pressure sensor 11' is functionally electrically coupled to the negative-pressure device 1. Accordingly, provision is made of an electric device-side pressure sensor interface 14', e.g. in the form of an electrical plug-in connector, instead of the fluidic device-side pressure sensor interface 14. A fluidic pressure sensor 11 in accordance with FIG. 1 can optionally be provided in addition thereto.

The invention claimed is:

1. A negative-pressure device for affixing a patient interface on a patient eye, said negative-pressure device comprising:

a negative-pressure generator and a device-side negative-pressure interface for fluidic coupling of the negative-pressure generator to a negative-pressure cavity of the patient interface via a negative-pressure fluidic connection line;

a fluidic pressure sensor and a device-side pressure sensor interface for coupling the fluidic pressure sensor to the patient interface via a pressure sensor fluidic connection line, wherein the pressure sensor fluidic connection line is different from the negative-pressure fluidic connection line; and a control unit operatively coupled to the negative-pressure generator and the fluidic pressure sensor, wherein the control unit is designed to actuate the negative-pressure generator for purposes of generating a negative pressure in the negative-pressure cavity and is furthermore designed to evaluate a pressure established by the fluidic pressure sensor.

2. The negative-pressure device as claimed in claim 1, wherein the control unit is designed to detect a faulty fluidic coupling of the negative-pressure cavity by detecting a deviation between the pressure established by means of the fluidic pressure sensor and a reference pressure or by detecting a reduction in the negative pressure as a function of time.

3. The negative-pressure device as claimed in claim 1, wherein the negative-pressure device comprises a second pressure sensor fluidically coupled to the device-side negative-pressure interface and operatively coupled to the control unit and wherein the control unit is designed to detect a faulty fluidic coupling of the negative-pressure cavity by means of a comparison of an established pressure with a second pressure established by the second pressure sensor.

4. The negative-pressure device as claimed in claim 1, wherein the negative-pressure device comprises a flow sensor fluidically coupled to the device-side negative-pressure interface and operatively coupled to the control unit, for purposes of establishing a fluid flow through the device-side negative-pressure interface.

5. The negative-pressure device as claimed in claim 1, wherein the negative-pressure device comprises a valve unit fluidically coupled to the device-side negative-pressure interface and the negative-pressure generator and operatively coupled to the control unit.

6. The negative-pressure device as claimed in claim 5, wherein the valve unit is designed to alternatively fluidically seal the device-side negative-pressure interface, fluidically couple the latter to the negative-pressure generator or fluidically couple said device-side negative-pressure interface with an equalization volume.

7. The negative-pressure device as claimed in claim 1, wherein the negative-pressure device comprises a patient interface coupler, wherein the patient interface coupler comprises both the device-side negative-pressure interface and the device-side pressure sensor interface.

* * * * *